United States Patent [19]

Boor et al.

[11] Patent Number: 4,482,494
[45] Date of Patent: Nov. 13, 1984

[54] PROCESS FOR PREPARING 17α-HYDROXY-PREGN-4-EN-3,20-DIONE

[75] Inventors: Anna Boor; Jozsef Toth; Tamas Szen; Laszlo Gabor; Piroska Major nee Feistner; Sandor Holly, all of Budapest, Hungary

[73] Assignee: Richter Gedeon Vegyeszeti Gyar R.T., Budapest, Hungary

[21] Appl. No.: 435,494

[22] Filed: Oct. 20, 1982

Related U.S. Application Data

[62] Division of Ser. No. 365,015, Apr. 2, 1982, Pat. No. 4,368,160.

[30] Foreign Application Priority Data

Apr. 16, 1981 [HU] Hungary ............................. 989

[51] Int. Cl.³ ................................................ C07J 5/00
[52] U.S. Cl. ................................................ 260/397.4
[58] Field of Search ........................................ 260/397.4

[56] References Cited

U.S. PATENT DOCUMENTS

| | | | |
|---|---|---|---|
| 2,964,537 | 12/1960 | Engelfried et al. | 260/397.4 |
| 3,880,895 | 4/1975 | Greenspan et al. | 260/397.4 |
| 4,039,669 | 8/1977 | Beyler et al. | 260/397.4 |
| 4,102,908 | 7/1978 | Hofmeister et al. | 260/397.4 |

FOREIGN PATENT DOCUMENTS

| | | | |
|---|---|---|---|
| 646287 | 8/1962 | Canada | 260/397.4 |
| 174982 | 12/1980 | Hungary | 26/397.4 |

Primary Examiner—Elbert L. Roberts
Attorney, Agent, or Firm—Karl F. Ross; Herbert Dubno

[57] ABSTRACT

The invention relates to a novel process for the preparations of pregnane derivatives of formula I,

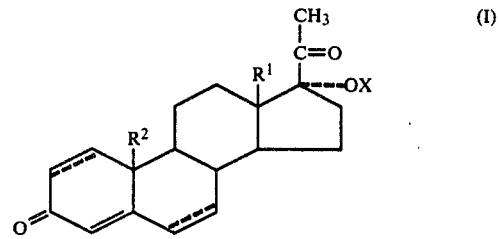

wherein
$R^1$ stands for a methyl or an ethyl group,
$R^2$ represents a hydrogen atom or a methyl group, and
X is a hydrogen atom or a formyl or acetyl group, and the bond indicated by a dotted and a continuous line stands for a single or a double bond beween the two neighboring carbon atoms.

According to the invention a trifluoroacetate ester of formula II,

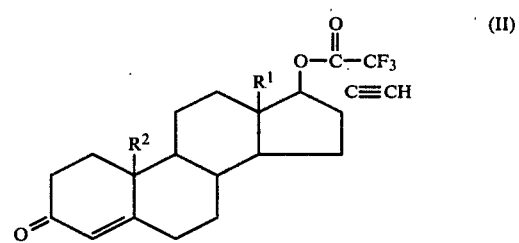

wherein $R^1$ and $R^2$ are as defined above, is reacted with formic acid or acetic acid in the presence of a catalytic amount of a mercury salt in a dipolar proton-free or basic solvent. The formyl or acetyl group being in the place of X can be split off in a way known per se.

The process provides a novel advantageous method for building up the pregnane side chain characteristic of corticoids.

1 Claim, No Drawings

PROCESS FOR PREPARING 17α-HYDROXY-PREGN-4-EN-3,20-DIONE

This application is a division of application Ser. No. 365,015, filed Apr. 2, 1982, now U.S. Pat. No. 4,368,160.

The invention relates to a novel process for preparing pregnane derivatives of formula I

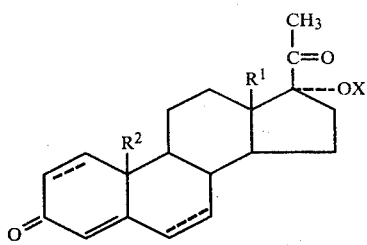

wherein
R¹ stands for a methyl or an ethyl group,
R² represents a hydrogen atom or a methyl group and
X is a hydrogen atom or a formyl or acetyl group, and the bond indicated by a dotted and a continuous line stands for a single or a double bond between the two neighboring carbon atoms.

The process according to the invention provides an advantageous novel method for building up the pregnane side chain characteristic of corticoids.

Processes for building up the pregnane side chain were already known earlier [Ber. 71, 1487 (1938); Ber. 72, 182 (1939); Ber. 97, 2011 (1964); Helv. Chim. Acta 22, 755 (1939); J. Am. Chem. Soc. 81, 5725 (1959); U.S. Pat. specification No. 4,041,055]. These solutions are, however, not at all or only hardly suitable for industrial use. This is due, among other reasons, to too many process steps, the low yields, the extreme reaction conditions and, in certain cases, the fact that the reagents to be used are difficult to treat or to obtain.

In the published German applications (Offenlegungsschrift) Nos. 2,140,291 and 2,230,286 the use of mercury salts as catalyst was proposed for enhancing the formation of the pregnane side chain. These processes starting from 17α-ethynyl-17β-sulfite esters do not provide, however, sufficient yields when higher amounts are to be prepared; at the same time the formation of isomeric 17α-pregnane-derivatives is inevitable.

A further-development of the reaction for the formation of the pregnane side chain under the catalytic effect of mercury salts is disclosed in the Hungarian patent specification No. 174,982. On using the 17-nitrate esters of 17α-ethynyl-17β-hydroxy-gonano as starting materials and mercury salts of lower carboxylic acids as catalysts, the nitrate esters are reacted in a dipolar proton-free medium or in a basic solvent with formic acid or acetic acid. According to the examples of the specification the corresponding 17α-formyloxy- or 17α-acetoxy-20-keto-pregnane derivative is obtained with a yield of from 44.1% to 83.0%. However, in a later published article [Ber. 111, 3086 (1978)] the inventors of this Hungarian patent described the preparation of the 17α-formyloxy-20-keto-pregnane-derivatives with the method according to the cited specification in a yield of only 50 to 70%, using the very difficult chromatographic isolation which is practically unsuitable for industrial purposes. Besides, the 17α-acetoxyprrogesterone could be isolated with a yield of only 6.4%, instead of a 40% yield disclosed in the patent specification, and in this article it is stated that the yield could not be increased even by adding hexamethyl phosphoric acid triamide and using a reaction time of 48 hours.

The above-mentioned process has numberous disadvantages, too. The taking place of side reactions is proved, beside the yields of medium degree, by the fact that, according to all the examples of the specification, the crude product has to be purified by chromatography on silicic acid gel which is a labor and solvent-consuming operation and its industrial realization is possible only with serious difficulties. The greatest disadvantage of the process resides, however, in the difficulty in preparing and using the 17α-ethynyl-17β-nitrate ester starting substance. Namely, on preparing the nitrate ester the reaction mixture has to be kept at a temperature of about −20° C. The yield is low; e.g. on starting from 17α-ethynyl-17β-hydroxy-androst-4-en-3-one the 17-nitrate ester can be prepared with a yield of only 66% [Ber. 111, 3086 (1978)]. The isolated nitrate esters are difficult to handle, they are often oily. unstable substances, at the same time their preparation and use raise safety problems, too. Thus, e.g. the 17α-ethynyl-17α-hydroxy-androst-4-en-3-one-17-nitrate-ester- which, among others, can be the intermediate product of prednisolone—tends to explode and, according to our examinations, it is more dangerous than the 2,4,6-trinitro-toluene (TNT) used definitely as explosive. Therefore, in contradiction to the disclosure of the Hungarian patent specification No. 174,982, the building up of the pregnane side chain via the 17-nitrate esters of the 17α-ethynyl-17α-hydroxysteroids seems not to be possible on an industrial scale.

This invention aims at working out an economical and industrially realizable process for building up the pregnane side chain by using 17α-ethynyl-17β-hydroxy-derivatives obtained as intermediates in steroid total syntheses.

The invention is based on the recognition that the 17-trifluoroacetate-esters of 17α-ethynyl-17β-hydroxy-gonans can be advantageously used for the preparation of the corresponding 17α-formyloxy- or 17α-acetoxy-20-keto-pregnane-derivatives since they provide the desired pregnane derivative with formic acid or acetic acid in the presence of a mercury salt in a dipolar proton-free or basic solvent with practically quantitative yields.

According to the process of the invention a trifluoroacetate ester of formula II,

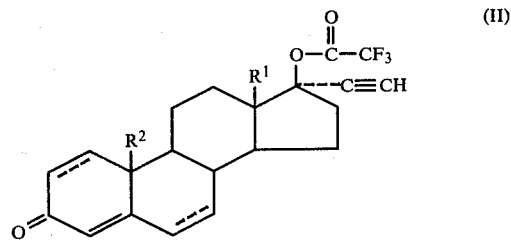

wherein R¹ and R² are as defined above, is reacted with formic acid or acetic acid in the presence of a catalytic amount of a readily dissociating mercury(I)- or mercury(II)-salt in a dipolar proton-free or basic solvent. If desired, the formyl or acetyl group being in the place of X can be split off in a way known per se.

The trifluoroacetate-esters of the formula II are novel compounds. They can be prepared by reacting a 17α-ethynyl-17β-hydroxy-compound of formula III,

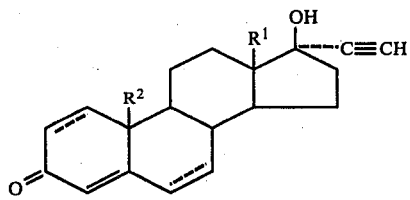

wherein R¹ and R² are as defined above, with trifluoroacetic anhydride in the presence of an acid-binding agent.

In the process according to the invention e.g. dimethyl formamide, dimethyl acetamide, hexamethyl phosphoric acid triamide or dimethyl-sulfoxide can be used as dipolar proton-free solvent and tertiary amines, e.g. triethyl amine, trimethyl amine or N-methyl-piperidine can be used as basic solvent.

The mercury salts of organic carboxylic acids, e.g. mercury(I)- and mercury(II)-acetate, mercury(II)-trifluoro- acetate, mercury(II)-benzoate, furthermore the readily dissociating inorganic mercury(I)- and mercury(II)-salts, e.g. mercury(I)-sulfate or mercury(II)-nitrate can be used as mercury salts.

The process according to the invention can be carried out at a temperature between 20° C. and 80° C., preferably at a temperature of 40° to 50° C. The use of higher or lower temperatures is not suitable because at temperatures above 80° C. side reactions can take place and at temperatures below 20° C. practically no reaction takes place.

If necessary, the reaction mixture can be diluted with an inert solvent, e.g. chloroform, dioxane or acetonitrile.

The starting compound of formula II of the process can be prepared also in situ in the above way; thus, the product of the trifluoroacetylation reaction is not separated but it is reacted in the reaction mixture itself with formic acid or acetic acid in the presence of a mercury salt, and the product is optionally treated-again without separating from the reaction mixture-with concentrated hydrochloric acid and methanol, whereby a 17α-hydroxy-20-oxo-pregnane derivative of formula I containing hydrogen in the place of X is directly obtained.

The above-mentioned recognition forming the basis of the invention is surprising because, according to literature data and our own experiments, other 17-esters of 17α-ethynyl-17β-hydroxy-gonans behave in a completely different way. According to the Hungarian patent specification No. 174,982, in a similar reaction of the 17-sulfite esters a considerable amount of the 17α-pregnane isomer is formed. According to the same specification, when using 17-nitrate esters the yield is only moderate, 44 to 83%, presumably due to side reactions.

At the same time, in the course of own experiments it has been found that the formic, acetic and monochloroacetic esters of 17α-ethynyl-17β-hydroxy-gonans are converted to 17α-pregnane derivatives in an analogous reaction with practically quantitative yield. Thus only the 17-trifluoro-acetate esters are suitable for the economical industrial preparation of pregnane derivatives having the side chain in a favourable steric position.

By the process according to the invention the 17α-formyloxy- or 17β-acetoxy-20-keto-pregnanes can be prepared with very good yields. At the same time the reaction conditions and the applied reagents ensure the economical industrial realization of the process. Besides, the industrial realization is not hindered by safety factors, either. From an industrial point of view it is a great advantage that on starting from a 17α-ethynyl-17β-hydroxy-gonan derivative, after the 17-trifluoroacetylation the 17α-acyloxy-20-keto-pregnane derivative can be directly obtained under the conditions of the claimed process, without the isolation of the ester. Moreover, the 17α-hydroxy-20-keto-pregnane derivative can be prepared without isolating the product by treating the reaction mixture with hydrochloric acid and methyl alcohol.

The process of the invention can be realized safely, easily and economically even an industrial scale. Thus, the synthesis of 17α-hydroxy-20-keto-pregnane derivatives can be realized by starting from 17 -oxo-androstanes prepared either by total synthesis or by decomposing the side chain of steroids (e.g. chloesterine, sitosterine, stigmasterine). These compounds are valuable intermediates of the active agents of numerous products which are very important in therapy, e.g. of the 17α-hydroxy-progesterone-capronate (Hormofort$^R$) exerting a gestagenic effect. Furthermore, the compounds according to the invention are important intermediates for the synthesis of Reichstein S and thereby for the preparation of corticoids exerting antiinflammatory effect, e.g. of hydrocortisone, prednisolone, 11β,17α-dihydroxy-21-(4-methylpiperazine-1-yl)-pregna-1,4-diene-3,20-dione (Depersolon$^R$) and triamcinolone.

The process of the invention is further illustrated with the aid of the following non-limiting examples.

EXAMPLE 1

400 ml of concentrated formic acid are admixed with 200 ml of hexamethyl phosphoric acid triamide under ice cooling. 40.8 (0.1 mole) of 17α-ethynyl-17β-trifluoroacetoxy-androst-4-en-3-one and 6.12 g of mercury(II)-acetate are added to the mixture, and after heating to 50 to 55° C. it is stirred at this temperature for 3 hours. The reaction mixture is poured onto 4 l of water, the separated product is filtered, washed with water and dried. 34.0 g (95.0%) of 17-formyloxy-pregn-4-ene-3,20-dione are obtained. After crystallizing from methyl alcohol the product melts at 217° to 219° C.; $[\alpha]_D^{20} = +87.0°$ (CHCl$_3$, C=1%).

EXAMPLE 2

400 ml of concentrated formic acid and 300 ml of triethyl-amine are admixed under ice cooling, then 40.8 g (0.1 mole) of 17α-ethynyl-17β-trifluoro-acetoxy-androst-4-en-3-one and 6.12 g of mercury(II)-acetate are added. The reaction mixture is stirred at a temperature of 55° C. for 4 hours, then it is poured onto 4 l of water. The separated product is filtered and dried. 34.3 g (95.8%) of 17α-formyloxy-pregn-4-en-3,20-dione are obtained. After crystallizing from methyl alcohol the product melts at 218° to 221° C.

EXAMPLE 3

40.8 g (0.1 mole) of 17α-ethynyl-17β-trifluoroacetoxy-androst-4-en-3-one are reacted as in Example 1 but instead of hexamethyl phosphoric acid triamide 300 ml of dimethyl formamide are used. In this way 33.6 g (93.8%) of crude 17α-formyloxy-pregn-4-en-3,20-dione are obtained. After crystallizing from methyl alcohol the product melts at 217° to 220° C.; $[\alpha]_D^{20} = +84.6°$ (CHCl$_3$, c=1%).

EXAMPLE 4

4.08 g (0.01 mole) of 17α-ethynyl-17β-trifluoroacetoxy-androst-4-en-3-one are reacted in a mixture of 40 ml of formic acid and 20 ml of hexamethyl phosphoric acid triamide in the way as described in Example 1 but instead of mercury(II)-acetate 0.62 g of mercury(II)-nitrate is used. After processing 3.35 g of 17α-formyloxy-pregn-4-ene-3,20-dione are obtained (93.6% of the theoretical yield). The crude product is crystallized from methyl alcohol. Melting point: 218° to 221° C.; $[\alpha]_D^{20} = +88.3°$ (CHCl$_3$, c=1%).

EXAMPLE 5

12 ml of acetic acid are admixed with 5 ml of dimethyl formamide under ice cooling, then 1.00 g (2.4 mmoles) of 17α-ethynyl-17β-trifluoroacetoxy-androst-4-en-3-one and 0.24 g of mercury(II)-acetate are added, and the reaction mixture is stirred at a temperature of 80° C. for 10 hours. Then the mixture is poured onto water, the separated crystalline substance is filtered, washed with water and dried. Thus 0.75 g (84.6%) of 17α-acetoxy-pregn-4-ene-3,20-dione is obtained. The product is crystallized from a mixture of acetone and hexane. Melting point: 240° to 244° C.; $[\alpha]_D^{20} = +69.3°$ (CHCl$_3$, c=1%).

EXAMPLE 6

10 ml of formic acid are admixed with 10 ml of dimethyl formamide under ice cooling, then 1.00 g (2.4 mmoles) of 17α-ethynyl-17β-trifluoroacetoxy-androsta-1,4-dien-3-one and 0.15 g of mercury(II)-acetate are added. The reaction mixture is stirred at a temperature of 60° C. for 10 hours, then the mixture is poured onto water. The separated substance is filtered, washed with water and dried. Thus 0.78 g (91.8%) of 17α-formyloxy-pregna-1,4-diene-3,20-dione is obtained. The crude product is crystallized from methyl alcohol. Melting point: 198° to 201° C.

EXAMPLE 7

12 ml of formic acid and 10 ml of dimethyl formamide are admixed under ice cooling, and 1.00 g (2.4 mmoles) of 17α-ethynyl-17β-trifluoroacetoxy-18-methyl-oestr-4en-3-one and 0.24 g of mercury(II)-acetate are added. The reaction mixture is heated to 45°to 50° C. and stirred at this temperature for 3 hours. The mixture is poured onto water, the separated crystalline substance is filtered, washed with water to neutral and dried. Thus 0.74 g of 17α-formyloxy-18-methyl-19- nor-pregn-4-ene-3,20-dione are obtained (84.3% of the theoretical yield). The product is crystallized from a mixture of acetone and ether. Melting point: 193° to 195°0 C.; $[\alpha]_D^{20} = +31.0°$ (CHCl$_3$, c=1%).

EXAMPLE 8

12 ml of formic acid are admixed with 10 ml of dimethyl formamide under cooling. 1 g (2.5 mmoles) of 17α-ethynyl-17β-trifluoroacetoxy-oestr-4-en-3-one and 0.27 g of mercury(II)-acetate are added to the mixture, then it is heated to 50° C. and stirred for 3 hours. After pouring it onto icy water the separated crystalline substance is filtered, washed and dried. Thus 0.80 g of 17α-formyloxy-19-nor-pregn-4-ene-3,20-dione are obtained (94.4% of the theoretical yield). The crude product is crystallized from methyl alcohol. Melting point: 201° to 203° C.; $[\alpha]_D^{20} = +32.0°$ (CHCl$_3$, c=1%).

EXAMPLE 9

To the solution of 3.12 g (0.01 mole) of 17α-ethynyl-17β-hydroxy-androst-4-en-3-one prepared with 31 ml of dimethyl-formamide 2.09 ml (0.015 mole) of trifluoroacetic anhydride are added at a temperature of 0° to 5° C. The mixture is stirred at the same temperature for 10 minutes, then 31 ml of formic acid and 0.46 g of mercury(II)-acetate are added. The reaction mixture is heated to 50°-55° C. and stirred at this temperature for 9 hours. After pouring onto water, filtration, washing and drying 3.40 g of 17α-formyloxy-pregn-4-ene-3,20-dione are obtained (94.9% of the theoretical yield). The crude product is crystallized from methyl alcohol. Melting point: 217° to 219° C.

EXAMPLE 10

Starting from 3.12 g (0.01 mole) of 17α-ethynyl-17β-hydroxy-androst-4-en-3-one one proceeds as described in Example 9 but after the reaction with mercury(II)-acetate the mixture is not poured onto water but the mixture of 24 ml of concentrated hydrochloric acid and 40 ml of methyl alcohol is added thereto. The reaction mixture is stirred at a temperature of 48° to 50° C. for 8 hours, then it is poured onto water. The separated product is filtered, washed with water and dried. Thus 2.70 g of 17α-hydroxy-pregn-4-ene-3,20-dione are obtained (82.1% of the theoretical yield). The crude product is crystallized from methyl alcohol. Melting point: 212°to 217° C.; $[\alpha]_D^{20} = +89°$ (CHCl$_3$, c=1%).

What we claim is:

1. A process for the preparation of a compound of the formula (I)

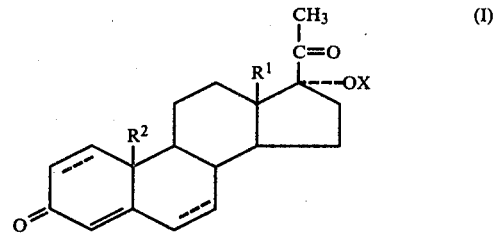

wherein

R$^1$ stands for a methyl or an ethyl group;

R$^2$ represents a hydrogen atom or a methyl group; and

X is a hydrogen, formyl, or acetyl; and the bond indicated by a dotted and a continuous line stands for a single or a double bond between the two neighboring carbon atoms, which comprises the steps of (a) acylating a compound of the formula (III)

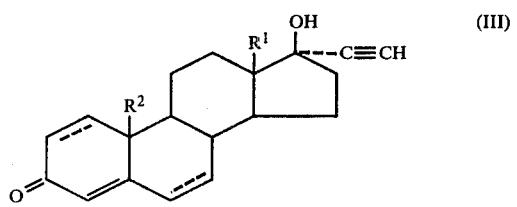

with trifluoroacetic acid in the presence of an acid binding agent at a temperature of 0° to 5° C.

to yield a compound of the formula (II)

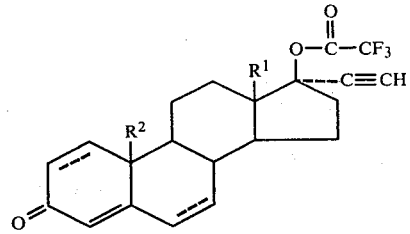

and
(b) reacting the compound of the formula (II) with formic acid to yield the compound of the formula (I) where X is formyl; or
(b₁) reacting the compound of the formula (II) with acetic acid to yield the compound of the formula (I) where X is acetyl; or
(b₂) following either (b) or (b₁), treating the reaction product with hydrochloric acid and methyl alcohol to yield the compound of the formula (I) where X is hydrogen.

* * * * *